United States Patent
Corradi et al.

(10) Patent No.: US 10,815,171 B2
(45) Date of Patent: Oct. 27, 2020

(54) PROCESS FOR THE PRODUCTION OF HIGH PURITY PARA-XYLENE AND HIGH PURITY TOLUENE

(71) Applicant: UOP LLC, Des Plaines, IL (US)

(72) Inventors: Jason T. Corradi, Arlington Heights, IL (US); Ryan D. Miller, Chicago, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 16/427,654

(22) Filed: May 31, 2019

(65) Prior Publication Data

US 2020/0048167 A1    Feb. 13, 2020

Related U.S. Application Data

(60) Provisional application No. 62/717,237, filed on Aug. 10, 2018.

(51) Int. Cl.
| | | |
|---|---|---|
| C07C 7/09 | (2006.01) |
| C07C 7/00 | (2006.01) |
| C07C 6/12 | (2006.01) |
| C07C 5/27 | (2006.01) |
| C07C 7/12 | (2006.01) |

(52) U.S. Cl.
CPC ............ *C07C 7/005* (2013.01); *C07C 5/2732* (2013.01); *C07C 6/123* (2013.01); *C07C 7/09* (2013.01); *C07C 7/12* (2013.01)

(58) Field of Classification Search
CPC .. C07C 7/005; C07C 7/04; C07C 7/09; C07C 7/12; C07C 7/13; C07C 6/123; C07C 5/2729; C07C 5/2732
See application file for complete search history.

(56) References Cited

U.S. PATENT DOCUMENTS

| | | | |
|---|---|---|---|
| 8,697,928 B2 | 4/2014 | Corradi | |
| 8,937,209 B2 | 1/2015 | Corradi | |
| 2013/0158330 A1 | 6/2013 | Corradi | |
| 2016/0046544 A1* | 2/2016 | Molinier | C07C 5/2732 585/319 |
| 2018/0093932 A1* | 4/2018 | Pednekar | C07C 5/277 |

OTHER PUBLICATIONS

Written Opinion from PCT Application No. PCT/US2019/046155, dated Oct. 22, 2019.
International Search Report from PCT Application No. PCT/US2019/046155, dated Nov. 21, 2019.

\* cited by examiner

*Primary Examiner* — In Suk C Bullock
*Assistant Examiner* — Jason Y Chong

(57) ABSTRACT

A process for the production of high purity toluene and para-xylene is described. More specifically, the process involves the production of high purity toluene produced via a light-desorbent selective adsorption process for para-xylene production, such as light desorbent para-xylene extraction, without the need for dedicated solvent extraction or olefin removal from the toluene stream.

16 Claims, 2 Drawing Sheets ns particularly pointed out in the appended claims.

PROCESS FOR THE PRODUCTION OF HIGH PURITY PARA-XYLENE AND HIGH PURITY TOLUENE

CROSS-REFERENCE TO RELATED APPLICATION

This application claims the benefit of U.S. Provisional Application Ser. No. 62/717,237 filed Aug. 10, 2018, the entirety of which is incorporated herein by reference.

FIELD

The present invention relates to a process for the production of high purity toluene. More specifically, the present invention relates to a process for the production of high purity toluene wherein high purity toluene can be produced via a light-desorbent selective adsorption process for para-xylene production, such as light desorbent para-xylene extraction, without need for dedicated solvent extraction or olefin removal from the toluene stream.

BACKGROUND

Aromatics complexes for para-xylene production also generate valuable byproducts including benzene and gasoline blending components. On occasion an on-purpose high-purity toluene byproduct may also be desired. However, toluene is generally recycled to extinction within the complex as it is converted to higher value para-xylene or benzene products, so it is not readily available at suitable purity within the complex. To achieve the high purity necessary for saleable toluene product, either the entire recycle toluene stream must be purified, or a dedicated processing route including solvent extraction of aromatics, olefin removal, and separate product distillation are necessary. It would be advantageous to produce a high-purity toluene product without need for some or all of these additional unit operations.

SUMMARY

The present disclosure describes a process for the production of high purity toluene wherein high purity toluene can be produced via a light-desorbent selective adsorption process for para-xylene production, such as light desorbent para-xylene extraction, without need for dedicated solvent extraction or olefin removal from the toluene stream. By high purity toluene, we mean a minimum of 99.9 wt % toluene.

In the foregoing, all temperatures are set forth in degrees Celsius and, all parts and percentages are by weight, unless otherwise indicated. Other objects, advantages and applications of the present invention will become apparent to those skilled in the art from the following detailed description and drawing. Additional objects, advantages and novel features of the examples will be set forth in part in the description which follows, and in part will become apparent to those skilled in the art upon examination of the following description and the accompanying drawing or may be learned by production or operation of the examples. The objects and advantages of the concepts may be realized and attained by means of the methodologies, instrumentalities and combinations particularly pointed out in the appended claims.

DETAILED DESCRIPTION

The following detailed description is merely exemplary in nature and is not intended to limit the application and uses of the embodiment described. Furthermore, there is no intention to be bound by any theory presented in the preceding background or the following detailed description.

Figure 1:
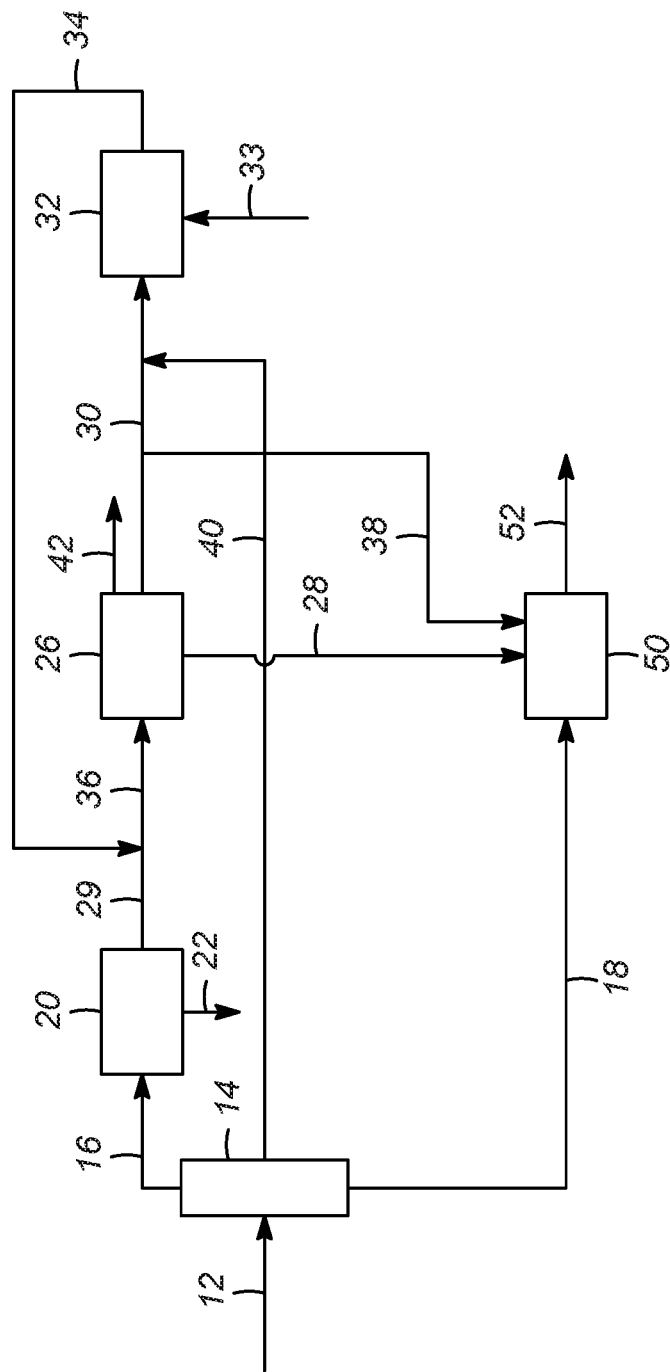
FIG. 1 illustrates an overview of a selective adsorption process with light desorbent.
Figure 2:
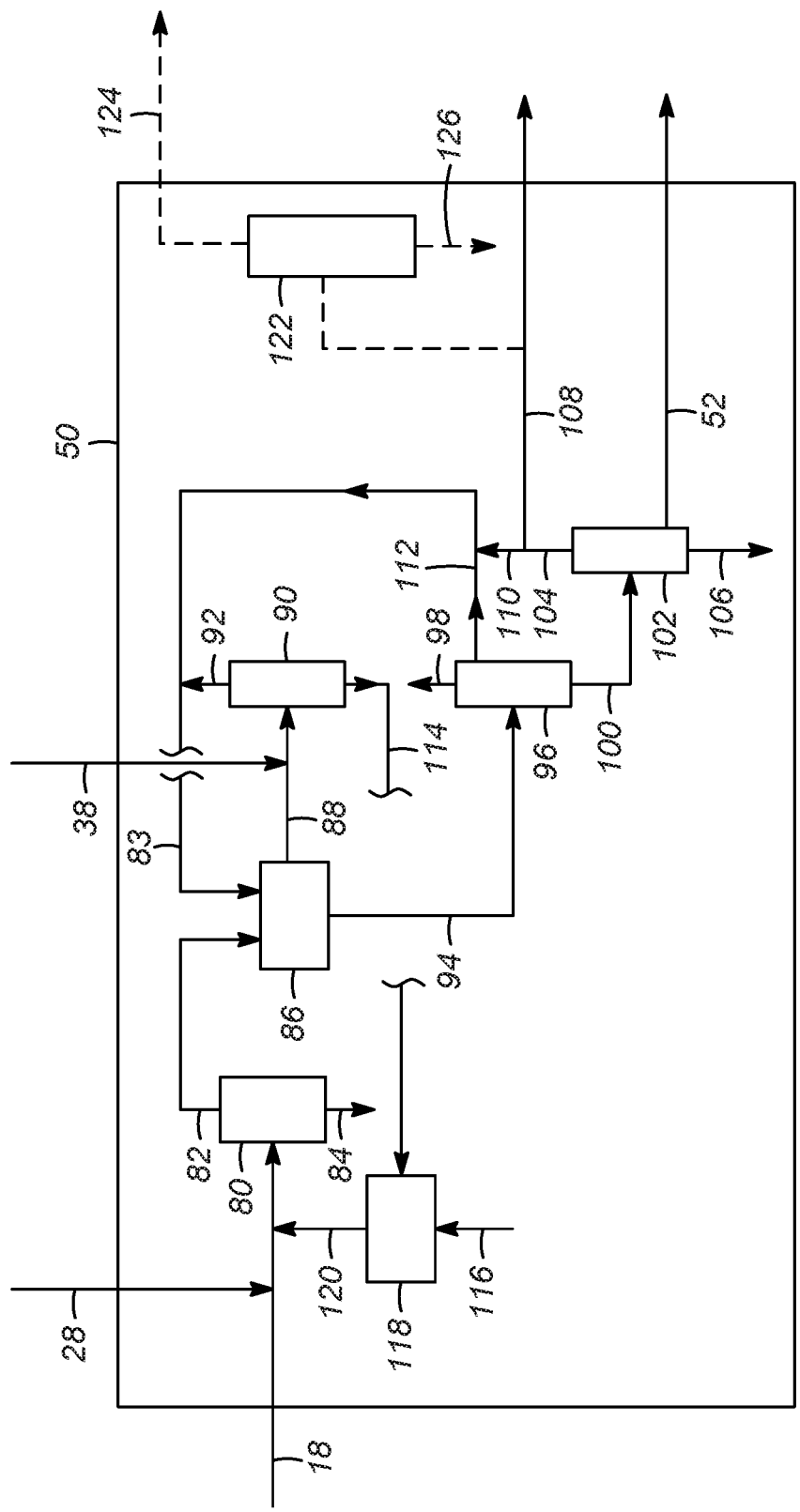
FIG. 2 illustrates a portion of the selective adsorption process of FIG. 1 showing the para-xylene recovery process with toluene product recovery.

The description of the process of this invention is presented with reference to FIGS. 1 and 2. FIGS. 1 and 2 are simplified diagrams of one embodiment of this invention and are not intended as an undue limitation on the generally broad scope of the description provided herein and the appended claims. Certain hardware such as valves, pumps, compressors, heat exchangers, instrumentation and controls, have been omitted as not essential to a clear understanding of the invention. The use and application of this hardware is well within the skill of the art.

High purity toluene can be produced via a light-desorbent selective adsorption process for paraxylene production, such as light desorbent para-xylene extraction, without the need for dedicated solvent extraction or olefin removal from the toluene stream. The solution is to withdraw the product toluene from within the light desorbent para-xylene extraction unit. More specifically, if the toluene product is sourced from the recycle toluene desorbent already separated from the para-xylene extraction stream, it will not contain undesirable olefin and non-aromatic species since these are rejected from the extract components during selective adsorption. As a result, no additional toluene extraction is required. Furthermore, the use of a two-stage extract column fractionation allows for more volatile toluene impurities to be effectively removed from the toluene product. A dedicated toluene product column is also considered, since the toluene product stream flowrate is anticipated to be an order of magnitude or two lower than a typical toluene recycle stream within the aromatics complex. That is, it is economically favorable to process the least amount of toluene necessary to satisfy the product target.

The various embodiments described herein relate to process for the production of high purity toluene. FIG. 1 depicts a simple block flow diagram of para-xylene production using selective adsorption with light desorbent or crystallization. A reformate feedstock 12 is fed to a reformate splitter 14 to separate a light overhead stream 16 comprising benzene, toluene, and co-boiling non-aromatics from a bottoms stream 18 comprising xylenes and heavier hydrocarbons.

The overhead stream 16 is directed to an aromatics extraction unit 20 (ED) to remove a raffinate stream 22 comprising non-aromatics. The extracted aromatics stream 24 comprising benzene and toluene from the aromatics extraction unit 20 is sent to in benzene/toluene fractionation column 26 where it is separated further to produce a bottoms stream 28 comprising C8+ aromatics, a benzene product stream 42, and a low-purity toluene stream 30 comprising toluene, xylenes, and trace levels of benzene. By low-purity toluene, we mean less than 99 wt % toluene.

The bottoms stream 28 is sent to a para-xylene separation and xylene isomerization zone 50 from which a high purity para-xylene product stream 52 is recovered either by selective adsorption or crystallization.

The low-purity toluene stream 30 is sent to a transalkylation (TA) unit 32 to react with stream 33 comprising C9 and C10 aromatics to create xylenes. The effluent 34 from the transalkylation unit 32 which comprises xylenes, heavier aromatics, and unreacted toluene and heavier aromatics (as well as lighter products such as benzene and fuel) is recycled to the benzene/toluene fractionation column 26.

An alternate flow scheme includes a third fraction removed from the reformate splitter 14 as a sidedraw stream 40. This sidedraw stream 40 is a low-purity toluene stream which is substantially free of benzene. It is sent directly to the TA unit 32, bypassing the aromatic extraction unit (ED) 20.

The low-purity toluene stream 30 from the benzene/toluene fractionation column 26 and low-purity toluene stream 40 from the reformate splitter 14 do not meet high-purity toluene standards. In order to obtain a high-purity toluene stream, these streams would require additional processing. Because they are large volume streams, such additional processing would be extremely expensive.

FIG. 2 depicts the separation of desorbent and para-xylene as part of the para-xylene separation and xylene isomerization zone 50. Within the para-xylene separation and xylene isomerization zone 50 there exists a purified toluene stream that meets high purity toluene requirements without further processing. This is due to the nature of the light desorbent system where high purity toluene desorbent is readily available.

The bottoms stream 28 comprising C8+ aromatics from the benzene/toluene fractionation column 26 is sent to a xylenes fractionation column 80 where it is separated into an overhead stream 82 comprising mixed xylenes and a bottoms stream 84 comprising C9+ aromatics. The bottoms stream 18 from the reformate splitter 14 can also be sent to the xylenes fractionation column 80.

The bottoms stream 84 can be sent to a heavy aromatics column (not shown) to be separated into an overhead stream comprising C9 and C10 aromatics and a bottoms stream comprising C11+ aromatics. The overhead stream from the heavy aromatics can be sent to the TA unit 32 as stream 33. The bottoms stream from the heavy aromatics column can be sent for use as fuel oil.

The overhead stream 82 from the xylenes fractionation column and toluene stream 83 are sent to an adsorbent chamber 86 comprising a para-xylene selective adsorbent. A stream 88 comprising about 50 wt % ortho-xylene, meta-xylene, and about 50 wt % low-purity toluene is withdrawn from the adsorbent chamber 86. There may also be some ethylbenzene and A9 aromatics in stream 88.

Stream 88 and a portion 38 of low-purity toluene stream 30 which provides make-up toluene for the desorption of para-xylene in the adsorbent chamber 86 are sent to raffinate column 90. Alternatively, the portion 38 could come from low-purity toluene stream 40. In this arrangement, it would bypass the ED unit 20 avoiding expensive and unnecessary extraction.

The raffinate overhead stream 92 comprising toluene is recycled to adsorbent chamber 86 as at least a portion of toluene stream 83.

An extract stream 94 comprising para-xylene and toluene desorbent is removed from the adsorbent chamber 86 and sent to a first para-xylene fractionation column 96 where it is separated into an overhead stream 98 comprising C6− compounds and a bottoms stream 100 comprising para-xylene and toluene. The overhead stream 98 may also contain water.

The bottoms stream 100 from the first para-xylene fractionation column 96 is sent to a second para-xylene fractionation column 102 where it is separated into a sidedraw stream 52 comprising the high purity para-xylene product, an overhead stream 104 comprising high purity toluene, and a bottoms stream 106 comprising C9+ aromatics.

A portion 108 of the overhead stream 104 from the second para-xylene fractionation column 102 can be recovered as the high purity toluene stream. Thus, a high purity toluene stream has been produced, and a portion may be diverted for sale as product without further separation.

One or more of a second portion 110 of the overhead stream 104 from the second para-xylene fractionation column 102 and a sidedraw stream 112 comprising toluene from the first para-xylene fractionation column 96 can be recycled to the adsorbent chamber 86 along with the raffinate overhead stream 92 forming toluene stream 83 for use in desorbing the para-xylene. The bottoms stream 114 comprising ortho-xylene and meta-xylene from the raffinate column 90 and hydrogen 116 can be sent to isomerization unit 118 for isomerization. The isomerate 120 can be sent to the xylenes fractionation column 80.

Alternately, a dedicated toluene column 122 may be installed for on-purpose toluene production, thereby allowing a degree of freedom to enable maximum paraxylene production without constraint from the high purity toluene product. It might be more cost effective to produce para-xylene without having to co-produce high purity toluene directly from the second para-xylene fractionation column 102. That is, some para-xylene in the overhead stream 104 of the second para-xylene fractionation column 102 might be economically beneficial. In this case, a portion 108 of the overhead stream 104 which contains toluene and a small amount of para-xylene is sent to a toluene column 122 where it is separated into an overhead stream 124 comprising high purity toluene and a bottom stream 126 comprising para-xylene.

While the invention has been described with what are presently considered the preferred embodiments, it is to be understood that the invention is not limited to the disclosed embodiments, but it is intended to cover various modifications and equivalent arrangements included within the scope of the appended claims.

Specific Embodiments

While the following is described in conjunction with specific embodiments, it will be understood that this description is intended to illustrate and not limit the scope of the preceding description and the appended claims.

A first embodiment of the invention is a process for producing high purity toluene and para-xylene in a para-xylene complex comprising separating an extract stream comprising para-xylene and toluene from an adsorbent chamber into an overhead stream comprising C6− compounds and a bottoms stream comprising para-xylene and toluene in a first para-xylene fractionation column; separating the bottoms stream from the first para-xylene fractionation column in a second para-xylene fractionation column into a sidedraw stream comprising high purity para-xylene, an overhead stream comprising toluene, and a bottoms stream comprising C9+ aromatics; recovering the sidedraw stream as a high purity para-xylene stream; and recovering at least a portion of the overhead stream from the second para-xylene fractionation column as a high purity toluene product stream. An embodiment of the invention is one, any or all of prior embodiments in this paragraph up through the first embodiment in this paragraph wherein the overhead stream from the second para-xylene fractionation column comprises high purity toluene. An embodiment of the invention is one, any or all of prior embodiments in this paragraph up through the first embodiment in this paragraph further comprising; separating the overhead stream from the second para-xylene fractionation column in a toluene fractionation column into an overhead stream comprising high purity toluene and a bottom stream comprising xylenes, and wherein the high purity toluene product stream comprises the overhead stream from the toluene fractionation column. An embodiment of the invention is one, any or all of prior embodiments in this paragraph up through the first embodiment in this paragraph further comprising introducing a mixed xylenes stream and a toluene stream into the adsorption chamber comprising a para-xylene selective adsorbent; and separating the mixed xylenes stream and the toluene stream into the extract stream and a stream comprising ortho-xylene, meta-xylene, and toluene. An embodiment of the invention is one, any or all of prior embodiments in this paragraph up through the first embodiment in this paragraph further comprising separating a stream comprising C8+ aromatics in a xylene fractionation column to form the mixed xylenes stream and a bottoms stream comprising C9+ aromatics. An embodiment of the invention is one, any or all of prior embodiments in this paragraph up through the first embodiment in this paragraph further comprising separating the stream comprising ortho-xylene, meta-xylene, and toluene and a low purity toluene stream in a raffinate column into a raffinate overhead stream comprising toluene and a raffinate bottom stream comprising ortho-xylene and meta-xylene, wherein the raffinate overhead stream comprises at least a part of the toluene stream. An embodiment of the invention is one, any or all of prior embodiments in this paragraph up through the first embodiment in this paragraph further comprising isomerizing the raffinate bottom stream to form an isomerate; and separating the isomerate in the xylene fractionation column. An embodiment of the invention is one, any or all of prior embodiments in this paragraph up through the first embodiment in this paragraph further comprising removing a sidedraw stream comprising toluene from the first para-xylene fractionation column, wherein the sidedraw stream comprises at least a portion of the toluene stream introduced into the adsorption chamber. An embodiment of the invention is one, any or all of prior embodiments in this paragraph up through the first embodiment in this paragraph wherein at least a portion of the overhead stream from the second fractionation column comprises at least a portion of the toluene stream into the adsorption chamber. An embodiment of the invention is one, any or all of prior embodiments in this paragraph up through the first embodiment in this paragraph further comprising separating a reformate feedstock into an overhead stream comprising benzene, toluene, and co-boiling non-aromatics and a bottoms stream comprising xylenes and heavier hydrocarbons in a reformate splitter; separating the overhead stream from the reformate splitter into an extracted aromatics stream comprising benzene and toluene and a raffinate stream comprising non-aromatics; separating the extracted aromatics stream into a benzene product stream, a low-purity toluene stream, and a bottoms stream comprising C8+ aromatics in a benzene/toluene fractionation column, wherein the bottoms stream from the benzene/toluene column forms at least a part of the stream separated in the xylene fractionation column; wherein a first portion of the low-purity toluene stream is the low-purity toluene stream introduced into the raffinate column; transalkylating a second portion of the low-purity toluene stream in a transalkylation reactor to produce and transalkylation effluent comprising xylenes, heavier aromatics, and unreacted toluene; and recycling the transalkylation effluent to the benzene/toluene fractionation column. An embodiment of the invention is one, any or all of prior embodiments in this paragraph up through the first embodiment in this paragraph wherein the bottoms stream from the reformate splitter comprises at least a portion of the stream separated in the xylene fractionation column. An embodiment of the invention is one, any or all of prior embodiments in this paragraph up through the first embodiment in this paragraph further comprising withdrawing a sidedraw comprising low-purity toluene from the reformate splitter; and introducing the sidedraw from the reformate splitter into the transalkylation reactor.

A second embodiment of the invention is a process for producing high purity toluene and para-xylene in a para-xylene complex, the process comprising separating a bottoms stream comprising C8+ aromatics from a benzene/toluene fractionation column in a xylenes fractionation column into an overhead stream comprising mixed xylenes and a bottoms stream comprising C9+ aromatics; introducing the overhead stream from the xylenes fractionation column into an adsorbent chamber comprising a para-xylene selective adsorbent; separating a stream comprising ortho-xylene, meta-xylene, and low-purity toluene from the adsorbent chamber and a portion of a low-purity toluene stream from the benzene/toluene fractionation column in a raffinate column into a raffinate overhead stream comprising toluene and a raffinate bottom stream comprising ortho-xylene and meta-xylene; introducing the raffinate overhead stream into the adsorbent chamber; removing an extract stream comprising para-xylene and toluene from the adsorbent chamber; separating the extract stream into an overhead stream comprising C6– compounds and a bottoms stream comprising para-xylene and toluene in a first para-xylene fractionation column; separating the bottoms stream from the first para-xylene fractionation column in a second para-xylene fractionation column into a sidedraw stream comprising high purity para-xylene, an overhead stream comprising toluene, and a bottoms stream comprising C9+ aromatics; recovering the sidedraw stream as a high purity para-xylene stream; and recovering at least a portion of the overhead stream from the second para-xylene fractionation column as a high purity toluene product stream. An embodiment of the invention is one, any or all of prior embodiments in this paragraph up through the second embodiment in this paragraph further comprising removing a sidedraw stream comprising toluene from the first para-xylene fractionation column; and combining the sidedraw stream from the first para-xylene fractionation column with the raffinate overhead stream. An embodiment of the invention is one, any or all of prior embodiments in this paragraph up through the second embodiment in this paragraph further comprising combining at least a second portion of the overhead stream from the second para-xylene fractionation column with the raffinate overhead stream. An embodiment of the invention is one, any or all of prior embodiments in this paragraph up through the second embodiment in this paragraph further comprising isomerizing the raffinate bottom stream to form isomerate; and introducing the isomerate into the xylenes fractionation column. An embodiment of the invention is one, any or all of prior embodiments in this paragraph up through the second embodiment in this paragraph further comprising separating the reformate feedstock into an overhead stream comprising benzene, toluene, and co-boiling non-aromatics, a bottoms stream comprising xylenes and heavier hydrocarbons in a reformate splitter, and optionally a sidedraw comprising low-purity toluene; feeding the bottoms stream from the reformate splitter to the xylenes fractionation column; and optionally introducing the sidedraw from the reformate splitter into the transalkylation reactor. An embodiment of the invention is one, any or all of prior embodiments in this paragraph up through the second embodiment in this paragraph further comprising separating the overhead stream into an extracted aromatics stream comprising benzene and toluene and a raffinate stream comprising non-aromatics; separating the extracted aromatics stream into a benzene product stream, the low-purity toluene stream, and the bottoms stream in the benzene/toluene fractionation column; transalkylating a second portion of the low-purity toluene stream in a transalkylation reactor to produce a transalkylation effluent comprising xylenes, heavier aromatics, and unreacted toluene; and recycling the transalkylation effluent to the benzene/toluene fractionation column. An embodiment of the invention is one, any or all of prior embodiments in this paragraph up through the second embodiment in this paragraph wherein the overhead stream from the second para-xylene fractionation column comprises high purity toluene. An embodiment of the invention is one, any or all of prior embodiments in this paragraph up through the second embodiment in this paragraph further comprising; separating the overhead stream from the second para-xylene fractionation column in a toluene fractionation column into an overhead stream comprising high purity toluene and a bottom stream comprising xylenes, and wherein the high purity toluene product stream comprises the overhead stream from the toluene fractionation column.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for producing high purity toluene and para-xylene in a para-xylene complex comprising:
    removing an extract stream comprising para-xylene and toluene from an adsorbent chamber;
    separating the extract stream into an overhead stream comprising C6-compounds and a bottoms stream comprising para-xylene and toluene in a first para-xylene fractionation column;
    separating the bottoms stream from the first para-xylene fractionation column in a second para-xylene fractionation column into a sidedraw stream comprising para-xylene, an overhead stream comprising toluene, and a bottoms stream comprising C9+ aromatics;
    recovering the sidedraw stream as a para-xylene stream; and
    recovering at least a portion of the overhead stream from the second para-xylene fractionation column as a high purity toluene product stream:
        wherein if the overhead stream from the second para-xylene fractionation column is high purity toluene, the recovering at least the portion of the overhead stream from the second para-xylene fractionation column as the high purity toluene product stream comprises recovering at least a portion of the overhead stream from the second para-xylene fractionation column as the high purity toluene product stream without further separation; and
    wherein if the overhead stream from the second para-xylene fractionation column is not high purity toluene, the recovering at least the portion of the overhead stream from the second para-xylene fractionation column as the high purity toluene product stream comprises separating the overhead stream from the second para-xylene fractionation column in a toluene fractionation column into an overhead stream comprising high purity toluene and a bottom stream comprising xylenes and recovering the overhead stream from the toluene fractionation column as the high purity toluene product stream.

2. The process of claim 1 further comprising:
introducing a mixed xylenes stream and a toluene stream into the adsorption chamber comprising a para-xylene selective adsorbent; and
separating the mixed xylenes stream and the toluene stream into the extract stream and a stream comprising ortho-xylene, meta-xylene, and toluene.

3. The process of claim 2 further comprising:
separating a stream comprising C8+ aromatics in a xylene fractionation column to form the mixed xylenes stream and a bottoms stream comprising C9+ aromatics.

4. The process of claim 3 further comprising:
separating the stream comprising ortho-xylene, meta-xylene, and toluene and a low purity toluene stream in a raffinate column into a raffinate overhead stream comprising toluene and a raffinate bottom stream comprising ortho-xylene and meta-xylene, wherein the raffinate overhead stream comprises at least a part of the toluene stream.

5. The process of claim 4 further comprising:
isomerizing the raffinate bottom stream to form an isomerate; and
separating the isomerate in the xylene fractionation column.

6. The process of claim 4 further comprising:
separating a reformate feedstock into an overhead stream comprising benzene, toluene, and co-boiling non-aromatics and a bottoms stream comprising xylenes and heavier hydrocarbons in a reformate splitter;
separating the overhead stream from the reformate splitter into an extracted aromatics stream comprising benzene and toluene and a raffinate stream comprising non-aromatics;
separating the extracted aromatics stream into a benzene product stream, a low-purity toluene stream, and a bottoms stream comprising C8+ aromatics in a benzene/toluene fractionation column, wherein the bottoms stream from the benzene/toluene column forms at least a part of the stream separated in the xylene fractionation column;
wherein a first portion of the low-purity toluene stream is the low-purity toluene stream introduced into the raffinate column;
transalkylating a second portion of the low-purity toluene stream in a transalkylation reactor to produce and transalkylation effluent comprising xylenes, heavier aromatics, and unreacted toluene; and
recycling the transalkylation effluent to the benzene/toluene fractionation column.

7. The process of claim 6 wherein the bottoms stream from the reformate splitter comprises at least a portion of the stream separated in the xylene fractionation column.

8. The process of claim 6 further comprising:
withdrawing a sidedraw comprising low-purity toluene from the reformate splitter; and
introducing the sidedraw from the reformate splitter into the transalkylation reactor.

9. The process of claim 2 further comprising:
removing a sidedraw stream comprising toluene from the first para-xylene fractionation column, wherein the sidedraw stream comprising toluene from the first para-xylene fractionation column comprises at least a portion of the toluene stream introduced into the adsorption chamber.

10. The process of claim 2 wherein at least a portion of the overhead stream from the second para-xylene fractionation column comprises at least a portion of the toluene stream into the adsorption chamber.

11. The process of claim 1 further comprising:
isomerizing the raffinate bottom stream to form isomerate; and
introducing the isomerate into the xylenes fractionation column.

12. The process of claim 1 further comprising:
separating the reformate feedstock into an overhead stream comprising benzene, toluene, and co-boiling non-aromatics, a bottoms stream comprising xylenes and heavier hydrocarbons in a reformate splitter, and optionally a sidedraw comprising low-purity toluene;
feeding the bottoms stream from the reformate splitter to the xylenes fractionation column; and
optionally introducing the sidedraw from the reformate splitter into the transalkylation reactor.

13. The process of claim 12 further comprising:
separating the overhead stream into an extracted aromatics stream comprising benzene and toluene and a raffinate stream comprising non-aromatics;
separating the extracted aromatics stream into a benzene product stream, the low-purity toluene stream, and the bottoms stream in the benzene/toluene fractionation column;
transalkylating a second portion of the low-purity toluene stream in a transalkylation reactor to produce a transalkylation effluent comprising xylenes, heavier aromatics, and unreacted toluene; and
recycling the transalkylation effluent to the benzene/toluene fractionation column.

14. A process for producing high purity toluene and para-xylene in a para-xylene complex, the process comprising:
separating a bottoms stream comprising C8+ aromatics from a benzene/toluene fractionation column in a xylenes fractionation column into an overhead stream comprising mixed xylenes and a bottoms stream comprising C9+ aromatics;
introducing the overhead stream from the xylenes fractionation column into an adsorbent chamber comprising a para-xylene selective adsorbent;
separating a stream comprising ortho-xylene, meta-xylene, and low-purity toluene from the adsorbent chamber and a portion of a low-purity toluene stream from the benzene/toluene fractionation column in a raffinate column into a raffinate overhead stream comprising toluene and a raffinate bottom stream comprising ortho-xylene and meta-xylene;
introducing the raffinate overhead stream into the adsorbent chamber;
removing an extract stream comprising para-xylene and toluene from the adsorbent chamber;
separating the extract stream into an overhead stream comprising C6-compounds and a bottoms stream comprising para-xylene and toluene in a first para-xylene fractionation column;
separating the bottoms stream from the first para-xylene fractionation column in a second para-xylene fractionation column into a sidedraw stream comprising para-xylene, an overhead stream comprising toluene, and a bottoms stream comprising C9+ aromatics;
recovering the sidedraw stream as a para-xylene stream; and
recovering at least a portion of the overhead stream from the second para-xylene fractionation column as a high purity toluene product stream;
wherein if the overhead stream from the second para-xylene fractionation column is high purity toluene, the recovering at least the portion of the overhead stream from the second para-xylene fractionation column as the high purity toluene product stream comprises recovering at least a portion of the overhead stream from the second para-xylene fractionation column as the high purity toluene product stream without further separation; and
wherein if the overhead stream from the second para-xylene fractionation column is not high purity toluene, the recovering at least the portion of the overhead stream from the second para-xylene fractionation column as the high purity toluene product stream comprises separating the overhead stream from the second para-xylene fractionation column in a toluene fractionation column into an overhead stream comprising high purity toluene and a bottom stream comprising xylenes and recovering the overhead stream from the toluene fractionation column as the high purity toluene product stream.

15. The process of claim 14 further comprising:
removing a sidedraw stream comprising toluene from the first para-xylene fractionation column; and
combining the sidedraw stream from the first para-xylene fractionation column with the raffinate overhead stream.

16. The process of claim 14 further comprising:
combining at least a second portion of the overhead stream from the second para-xylene fractionation column with the raffinate overhead stream.

* * * * *